United States Patent [19]
Dawson et al.

[11] Patent Number: 5,741,771
[45] Date of Patent: Apr. 21, 1998

[54] THROMBOLYTIC COMPOSITION

[75] Inventors: Keith Martyn Dawson; Lars Michael Wood; Michael Berisford Comer, all of Oxford, United Kingdom

[73] Assignee: British Biotech Pharmaceuticals Ltd., England

[21] Appl. No.: 750,711

[22] PCT Filed: Jun. 14, 1995

[86] PCT No.: PCT/GB95/01388

§ 371 Date: Mar. 18, 1997

§ 102(e) Date: Mar. 18, 1997

[87] PCT Pub. No.: WO95/35117

PCT Pub. Date: Dec. 28, 1995

[30]     Foreign Application Priority Data

Jun. 17, 1994 [GB] United Kingdom ............... 9412131

[51] Int. Cl.$^6$ ..................... A61K 38/49; A61K 38/48
[52] U.S. Cl. ................. 514/2; 514/17; 435/217; 435/212; 435/214; 530/324; 530/329
[58] Field of Search ................. 514/2, 17; 530/324, 530/329

[56]              References Cited

U.S. PATENT DOCUMENTS

| 4,996,050 | 2/1991  | Tsukada et al. ............ 424/92.2 |
| 5,637,492 | 6/1997  | Dawson et al. ............ 435/217 |
| 5,645,833 | 7/1997  | Dawson et al. ............ 424/94.64 |
| 5,688,664 | 11/1997 | Dawson et al. ............ 435/69.2 |

FOREIGN PATENT DOCUMENTS

| 94/01128 | 1/1994 | WIPO . |
| 95/12407 | 5/1995 | WIPO . |

OTHER PUBLICATIONS

Dawson et al. J. Biol. Chemistry, 269: 15989–15992, Jun. 1994.

*Primary Examiner*—Cecilia J. Tsang
*Assistant Examiner*—Michael Borin
*Attorney, Agent, or Firm*—Banner & Witcoff, Ltd.

[57]             ABSTRACT

The invention disclosed relates to thrombolytic combination therapy by the administration of an agent capable of activating native plasminogen, and a non-native plasminogen analogue which is cleavable by native thrombin to generate plasmin activity.

5 Claims, No Drawings

THROMBOLYTIC COMPOSITION

This invention relates to products and methods for improved thrombolytic treatment of patients having, or at risk of developing, a thrombus or thrombi. In particular, the invention relates to thrombolytic combination therapy by the administration of an agent capable of activating native plasminogen, and a non-native plasminogen analogue which is cleavable by native thrombin to generate plasmin activity.

BACKGROUND OF THE INVENTION

Plasminogen Activators

Agents capable of activating native plasminogen are known and are in use in thrombolytic therapy, are in clinical trial or have been proposed for that purpose. Examples of such compounds include tissue-type plasminogen activator (tPA), urokinase, streptokinase, and desmodus salivary plasminogen activator (DSPA). Intravenous treatment with tPA and streptokinase has been successful in reducing mortality from acute myocardial infarction.

Despite this success, it is widely recognised that thrombolysis has major limitations which are due to the shortcomings of the agents available (reviewed by Marder and Sherry, New England Journal of Medicine 1989, 318: 1513–1520). For example, for tPA these are its rapid elimination from the body and its relative lack of thrombus specificity at clinically useful doses. The rapid clearance of tPA means that a large quantity of the protein has to be given by intravenous infusion, delaying the start of therapy until the patient is admitted to hospital. A further problem associated with the rapid clearance of tPA is that reocclusion of the reperfused blood vessel commonly occurs when tPA administration is stopped. Finally, the relative lack of thrombus specificity of therapeutic doses of tPA produces a risk of haemorrhage. Risk of haemorrhage is a problem common to current thrombolytics because they are not thrombus specific at clinically useful doses and they activate plasminogen to produce plasmin in the general circulation.

Urokinase has a similar rapid plasma clearance and also requires administration by continuous infusion.

Many attempts have been made to increase the half-life of tPA to overcome its rapid clearance, but tPA variants in clinical development appear to be cleared only 3–5 times more slowly than tPA (Thromb. Haemostas. 66:569–574, 1991; Thromb. Haemostas. 70:307–312, 1993); the plasma half-life of tPA is around five minutes in man (Bounameaux et al. in: "Contemporary issues in Haemostasis and Thrombosis" vol 1 p5–91, 1985. Collen et al. eds, Churchill Livingstone). These tPA variants may well allow bolus administration and/or dose reduction but they are unlikely to remain in circulation long enough to be effective in preventing reocclusion. They are also unlikely to reduce the haemorrhagic risk significantly, and it may increase due to persistence in the circulation.

Another approach to improving the clinical efficacy of plasminogen activators is via adjunctive therapy with anti-coagulant and antiplatelet agents. There has been limited success in improving the therapeutic efficiency of tPA with the adjunct use of heparin and aspirin. However, such a therapeutic regime still has limitations of a 15–20% rate of failure to recanalize the infarct-related artery and by a reocclusion rate of 5–10%. As a result, the reinfarction rate at 30 days is 4–6%, cardiogenic shock and congestive heart failure occur in 5–7% and 15–17% of patients, respectively, and mortality is in the range of 5–8% (Am. J. Cardiol. 75:7–13 1995). Both the initial failure of thrombolysis and reocclusion despite the use of heparin and aspirin are thought to be the result of ongoing thrombin activity. Hence, more potent and selective agents are under investigation. Hirudin is a potent inhibitor of thrombin which, in animal models has been shown to be superior to heparin in decreasing platelet deposition and thrombus formation (Circulation 79: 657–665, 1989) and in models of coronary thrombosis has been shown to both speed thrombolysis and decrease reocclusion (Circulation 83:1048–1056 and Circulation Research 70:829–834, 1992). U.S. Pat. No. 4,944,943 discloses the use of thrombolytic agents such as tPA and antithrombotic agents, hirudin being the only suggested example, for adjunctive therapy. U.S. Pat. No. 5,126,134 discloses the use of plasminogen activator such as tPA and hirudin, for adjunctive therapy. However, three clinical trials investigating hirudin as an adjunct to tPA were stopped in 1994 because of a high incidence of bleeding (Circulation 90:1624–30, 1631–37 and 1638–42, 1994). In addition, these trials investigated a higher heparin dose than the previous norm and found that it too was associated with an increased haemorrhage incidence. Therefore it appears that intensification of adjunct antithrombotic therapy using agents which inhibit thrombin activity results in an unacceptable increase in bleeding.

Thrombin Activatable Plasminogen Mutants

Patent publications WO 91/09118 and WO 94/10318 (both British Bio-technology Ltd) describe a new approach to the treatment of thrombotic conditions, based on the use of mutants of plasminogen which are activated to generate plasmin or plasmin-like activity by cleavage by an enzyme which is itself involved in the natural clotting cascade, particularly thrombin. One advantage of such agents lies in their thrombus specificity. Since activation occurs on exposure to thrombin, which is particularly concentrated at the site of the thrombus, thrombolytic plasmin activity is generated where it is required, thereby reducing the risk of systemic activation and haemorrhage. It is to be expected that such compounds will have an antithrombotic effect also, because the tendency to thrombus formation will be counteracted by the thrombolytic plasmin activity generated by thrombin cleavage of the agent at that site. Natural Glu-plasminogen has a plasma half-life of 2.2 days (Thromb. Haemostas. 43:77–89 1980), thus prolonged persistence in the circulation confers a further advantage on thrombin-activatable plasminogen which complements the thrombus selectivity of its action.

The potency of the thrombin activatable plasminogen mutants of WO 91/09118 and WO 94/10318 may be enhanced by the further mutation disclosed in WO 94/03614 (British Bio-technology Ltd) which is designed to introduce resistance to antiplasmin, the cognate serine protease inhibitor of plasmin.

BRIEF DESCRIPTION OF THE INVENTION

This invention is based on the finding of the present inventors that thrombin activatable plasminogen analogues of the kind referred to above are capable of increasing the thrombolytic activity of plasminogen activating agents such as tPA without significantly increasing systemic plasmin production and therefore the risk of haemorrhage. This finding makes available a new more effective thrombolytic therapy by permitting bolus administration of the plasminogen activator and thus the earlier start of therapy; by reducing the effective dose of the plasminogen activator required, thereby reducing the haemorrhagic risk; and by reducing the incidence of reocclusion of opened vessels by reforming thrombi.

DETAILED DESCRIPTION OF THE INVENTION

According to the present invention there is provided a product containing a plasminogen activator and a thrombin-activatable plasminogen analogue, for simultaneous, separate or sequential use in thrombolytic therapy.

The invention also includes a method of treating a patient in need of thrombolytic or antithrombotic therapy, which comprises the simultaneous, separate or sequential intravenous administration of effective amounts of a plasminogen activator and a thrombin-activatable plasminogen analogue.

According to another aspect of the invention there is provided for the use of a thrombin-activatable plasminogen analogue in the preparation of an agent for:

a) treating a patient undergoing thrombolytic therapy with a plasminogen activator; and/or b) reducing the effective dose of a plasminogen activator required for a patient undergoing thrombolytic therapy with said plasminogen activator; and/or c) reducing the risk of haemorrhage in patients undergoing thrombolytic therapy with a plasminogen activator.

Such adjunct antithrombotic therapy can be used for the treatment of acute vascular diseases such as: myocardial infarct, stroke, unstable angina, pulmonary embolism, deep vein thrombosis, peripheral arterial occlusion, extracorporeal circulation, arteriovenous shunts and other venous thromboses to produce accelerated removal of pathological thrombus.

By the term "plasminogen activator" is meant a compound which activates plasminogen to generate plasmin-type thrombolytic activity. Examples of such compounds include those which directly cleave plasminogen to generate plasmin, such as tPA, DSPA, urokinase, and mutants of these proteins having sequence changes which do not destroy their ability to cleave plasminogen to release plasmin, as well as compounds which indirectly activate plasminogen, such as streptokinase, which forms a complex with plasminogen causing conformational changes which allow the complex to cleave plasminogen molecules to release plasmin.

By the term "thrombin-activatable plasminogen analogue" is meant a molecule differing from wild type plasminogen by having sequence changes which render the molecule cleavable by thrombin to release plasmin or a molecule substantially homologous to plasmin which retains plasmin-type activity. Thrombin-activatable plasminogen analogues are inefficiently activated by plasminogen activators when compared to natural plasminogen. The thrombin-activatable plasminogen analogues may also have sequence changes relative to wild type plasminogen which either have no effect on the thrombin-cleavability of the molecules and the plasmin activity of the cleavage product, or confer an additional benefit on the molecules while retaining thrombin-cleavability and the plasmin activity of the cleavage product, for example mutations which confer antiplasmin resistance as described in WO 94/03614.

Thrombin-activatable plasminogen analogues are disclosed in the British Bio-technology patent publications referred to above. The mutations which render the molecule cleavable by thrombin to generate plasmin activity, are preferably at or near the position in the molecule corresponding to the natural cleavage site of wild type plasminogen. In that connection, plasminogen was numbered as a result of the protein sequencing studies of Sottrup-Jensen et al. (in: Atlas of Protein Sequence and Structure (Dayhoff, M.O., ed.) 5 suppl. 3, p.95 (1978)) which indicated that plasminogen was a 790 amino acid protein and that the site of cleavage was the Arg(560)-Val(561) peptide bond. However, a suitable plasminogen cDNA useful as an intermediate in the synthesis of thrombin-activatable plasminogen analogues is that isolated by Forsgren et al (FEBS Letters 213:254–260 (1987)), which codes for a 791 residue protein with an extra Ile at position 65. In this specification, the numbering of the amino acids in plasminogen corresponds to that of the Forsgren cDNA.

The presently preferred plasminogen activator for use in the present invention is tPA, but "second generation tPAs" such as that known as BM 06.022 (Martin. U. et al. Thromb. Haemostas. 66:569–574, 1991) or that known as T103N.KHRR296–299AAAA (Paoni N.F. et al. Thromb. Haemostas. 70:307–312, 1993) may become preferred as and when approved for human therapy by the regulatory authorities.

Presently preferred thrombin-activatable plasminogen analogues for use in the present invention include those disclosed in WO 94/10318, which have a cleavage site sequence P4-P3-Pro-Arg-P1'-P2' where P3 is a basic amino acid residue, P4 is a hydrophobic amino acid residue and each of P1' and P2' is independently a non-acidic amino acid residue, said site being cleavable by thrombin between Arg and P1'. A particularly preferred thrombin-activatable plasminogen analogue for use in the invention is BB-10153, as described in example 2 of WO 94/10318, which is a plasminogen analogue in which, relative to wild type plasminogen, the amino acid residues Pro(559), Gly(560) are replaced by Thr-Thr-Lys-Ile-Lys-Pro, and Val(562) is replaced by Ile to produce a cleavage Iccp cleavable by thrombin; and two additional amino-acid substitutions Glu606 to Lys and Glu623 to Lys serve to impair binding of α2-antiplasmin.

In the products of the invention, the plasminogen activator and the thrombin-activatable plasminogen analogue are, for reasons of regulatory requirements and/or product quality control, preferably packaged separately in unit dose form, particularly for separate intravenous bolus injection. Standard injectable protein formulation technology enables the preparation of suitable unit dose formulations. The unit dose concentration of tPA will generally be in the range of 0.05–1.5 mg/kg body weight, preferably 0.1–0.5 mg/kg body weight, and the unit dose concentration of thrombin-activatable plasminogen analogue will generally be in the range of 0.1–5 mg/kg body weight, preferably 0.5–3 mg/kg body weight, more preferably 2 mg/kg body weight.

The maximum thrombin-activatable plasminogen analogue BB-10153 dose for man will generally be no more than 5 mg/kg.

As an alternative, the products of the invention may contain single unit doses of a mixture of the plasminogen activator and the thrombin-activatable plasminogen analogue, providing the formulation technology employed for its preparation ensures satisfactory stability and preservation of potency of the two components.

For the treatment of human patients, as an individual therapeutic, tPA was originally given as a 100 mg dose by intravenous infusion over 3 hours. This has now been superseded by an accelerated regime comprising an intravenous bolus dose of 15 mg followed by an intravenous infusion of 0.75 mg/kg of body weight over a 30 minute period (maximum 50 mg) and then an infusion of 0.5 mg/kg over 60 minutes (maximum 35 mg) (J. Am. Coil. Cardiol. 14:1566–1569, 1989 and N. Eng. J. Med. 329:673–682, 1993). tPA is not effective as a single i.v. bolus although it has recently been reported to be effective as two 50 mg i.v. bolus injections (J. Am. Coil. Cardiol.23:6–10, 1994). Reteplase (BM 06.022), long-acting tPA variant, has been administered as a double intravenous bolus of 10 million units (MU) followed 30 minutes later by 5 MU (Am. J. Cardiol. 72:518–524, 1993).

Streptokinase is administered as a 1.5 million unit dose by intravenous infusion over 1 hour.

The effective dosages of the plasminogen activator and thrombin activatable plasminogen analogues for administration can, based on the knowledge of current dosages and the potential reduction in tPA dose possible, be determined by the physician.

The inventors have discovered, from animal studies, that a 3-fold or more reduction in tPA dose is generally possible with the adjunct thrombin-activatable plasminogen analogue BB-10153, both agents given as an i.v. bolus. A similar reduction would be expected using other plasminogen activators. Thrombin-activatable plasminogen analogue adjunct administration may therefore allow the plasminogen activator agents to be given as a single bolus.

The maximum tPA dose in any current regime is 100 mg. By co-administration of a thrombin activatable plasminogen analogue the effective total tPA dose may be reduced to 80 mg, and preferably 70 mg, 60 mg, 50 mg, 40 mg, 35 mg, 30 mg 20 mg or 10 mg.

By co-administration of a thrombin activatable plasminogen analogue the effective total Reteplase tPA dose may be reduced to 12 MU, and preferably 10 MU, 8 MU, 7 MU, 6 MU, 5 MU, 4 MU, 3 MU, 2 MU or 1.5 MU. A similar total dose reduction may be achieved for the other "second generation tPAs" including that known as T103N .KH RR296–299AAAA.

By co-administration of a thrombin activatable plasminogen analogue the effective total streptokinase dose may be reduced to 1.2 MU, and preferably 1 MU, 0.8 MU, 0.7 MU, 0.6 MU, 0.5 MU, 0.4 MU, 0.3 MU, 0.2 MU or 0.15 MU.

Where the plasminogen activator and the thrombin-activatable plasminogen analogue are administered separately each by intravenous bolus injection, the order of administration is not critical. It may be preferable to administer the plasminogen activator first, followed by the thrombin-activatable plasminogen analogue.

Where the thrombin-activatable plasminogen analogue and tPA agents are administered separately, it is contemplated that the the first agent may be administered 1–30 minutes, preferably about 10 minutes, more preferably about 5 minutes, after administration of the first agent.

Administration of the plasminogen activator and the thrombin-activatable plasminogen analogue may also be by intravenous infusion, either from separate sources of the two components or (again providing the formulation technology employed for its preparation ensures satisfactory stability and preservation of potency of the two components) from a single source of the mixed components.

Simultaneous administration may be affected using a devise capable of administering two substances simultaneously. Alternatively, simultaneous administration is also contemplated to include the administration of either the thrombin-activatable plasminogen analogue or tPA first, and the other component may be administered immediately afterwards. "immediately" in this context meaning any period of time up to one minute after administration of the first component.

Alternatively, administration of either the plasminogen activator or the thrombin-activatable plasminogen analogue may be by intravenous infusion and the other by intravenous bolus injection.

One embodiment of the present invention is illustrated in the following non-limiting example.

EXAMPLE

Preparation of a thrombin-activatable plasminogen analogue

The design, construction, expression and purification of the thrombin-activatable plasminogen analogue BB-10153 is described in WO 94/10318.

BB10153 is a plasminogen analogue in which the amino acid residues Pro(559), Gly(560) are replaced by Thr-Thr-Lys-Ile-Lys-Pro, and Val(562) is replaced by Ile to produce a cleavage loop cleavable by thrombin; two additional amino-acid substitutions Glu606 to Lys and Glu623 to Lys serve to impair binding of α2-antiplasmin.

Biological testing of Adjunctive effects of Intravenous tPA and BB-10153

The thrombolytic activities of tPA and thrombin activatable plasminogen BB-10153 were measured in a rabbit arterial thrombosis model in which thrombus formation in the femoral artery is induced by insertion of a coil of copper wire (copper is a potent stimulus for thrombus formation). Blood flow was monitored just distal to the coil by an ultrasonic flow probe and meter.

Male New Zealand White rabbits, 2.5–3.0 kg, were anaesthetised by intravenous injection (ear vein) with a loading dose of 35 mg/kg of a 17.5 mg/ml pentobarbitone solution. Once the venous cannula was in place pentobarbitone was infused throughout the experiment at 18 mg/kg/hr (infusion rate of 2 ml/hr). The trachea of the anaesthetised rabbit was cannulated to allow the animal to be artificially respired. The end tidal CO2 was set to 6% and the inspired air was enriched with oxygen. Both jugular veins were cannulated, one for the anaesthetic infusion and the other for bolus doses of test compounds. The left carotid artery was cannulated to record blood pressure and heart rate.

The femoral artery from both limbs was dissected free from surrounding tissue making sure no side branches were tied. A laparotomy was performed and the peritoneum opened above the position where the aorta bifurcates into the lilac arteries. A flow probe (2SB Transonic) was placed on the left femoral artery distal to the lateral circumflex artery and superficial epigastric artery (approx 2–3 cm distal to the epigastric). Then approx. 5 ml of bicarbonate was given to correct any acidosis. A blood sample was taken to check the pH (7.35–7.45) and the blood gases $pO_2$ (100–120 mmHg) and pCO2(35–45 mmHg). A copper coil made from 10 turns of 0.5 mm diameter wire wrapped around a 21 gauge needle was used to induce a thrombus. The coil was positioned in the left femoral artery just distal to the lateral circumflex artery and proximal to the flow probe by cannulation of the right femoral artery. Branches between the coil and probe were tied. A cannula was used to advance the coil up into the right lilac artery and then into the aorta where the blood carries it down to the left lilac artery to the femoral artery. The coil is finally positioned using forceps. Blood flow was monitored just distal to the coil in the femoral artery by an ultrasonic flow probe and meter. Blood flow through the left femoral artery ceased within 5 minutes of placing the coil in the vessel and treatment started 30 minutes after cessation of flow. For the combined treatment, BB-10153 was given first as an intravenous bolus injection and was followed 5 minutes later by tPA, also given as a bolus. 1.0 ml blood samples were taken from a carotid artery for analysis before and at 0.5, 1, 2, 3 and 4 hours after drug administration. The samples were anticoagulated with 3.8% w/v trisodium citrate (1 part in 10). The samples were spun at 14000 rev/min for 10 minutes and the plasma was then used for haemostatic protein determinations (see Methods).

Thrombolytic activity of tPA tPA (Actilyse, purchased from Boehringer Ingelheim) at 3 mg/kg produced prolonged reperfusion in 4/6 animals and short periods of reperfusion in the remaining 2. tPA at 1 mg/kg induced significant periods of reperfusion in 2/8 animals but there was no reperfusion in the other 6. tPA at 0.3 mg/kg did not induce any significant reperfusion.

Thrombolytic activity of BB-101.53

BB-10153 did not induce reperfusion of the occluded femoral artery when administered at doses up to 4 mg/kg.

Thrombolytic activity of combined treatment with tPA and BB-10153

The thrombolytic potency of tPA was increased significantly by co-administration of BB-1 0153. The combination of 1 mg/kg tPA and 2 mg/kg BB-10153 induced prolonged reperfusion in 4/6 animals, a significant but shorter reperfusion in 1 animal and several short periods of flow in 1. This pattern was similar to that produced by 3 mg/kg tPA. The combination of 0.3 mg/kg tPA and 2 mg/kg BB10153 induced substantial periods of flow in 3/4 animals,

Effect of tPA and BB-10153 on plasma α2-antiplasmin and fibrinogen levels

Increasing the thrombolytic potency of tPA by co-administration of BB-10153 was not accompanied by a significant increase in the systemic generation of plasmin. tPA at 3 mg/kg produced marked systemic plasmin generation as evidenced by reduction of the plasma $\alpha$2-antipiasmin ($\alpha$2-PI) level to less than 20% of control and reduction of the plasma fibrinogen level to approximately 25% of control. tPA at 1 mg/kg reduced the $\alpha$2-PI and fibrinogen levels to around 60% and 75% of control respectively. BB-10153 at 2 mg/kg had no effect on plasma $\alpha$2-PI and fibrinogen levels. The combination of 1 mg/kg tPA and 2 mg/kg BB-10153 produced only a minor increase in systemic plasmin activity compared to that produced by 1 mg/kg tPA alone.

tPA at 0.3 mg/kg had little effect on the $\alpha$2-PI and fibrinogen levels and this was unchanged with the thrombolytic combination of 0.3 mg/kg tPA and 2 mg/kg BB10153.

METHODS

Haemostatic proteins

All determinations were performed on an ACL300R coagulometer from Instrumentation Laboratories; the coagulometer was supplied with a PC and relevant software (Research software). All reagents and kits for the coagulation tests were supplied by Instrumentation Laboratories, $\alpha$2-antiplasmin the assay was performed using the standard kit supplied for the coagulometer and the default settings for the antiplasmin test.

Fibrinogen

A modification of the Clauss method was used (Clauss. A, Acta Haematol. 17:237 1957) A calibration curve was created using calibration plasma (the reciprocal of the fibrinogen concentration vs time to clot). Plasma for the calibration curves was obtained from Instrumentation Laboratories (IL). The concentrations were 2.95, 1.475, 0.98, 0.7375, 0.59 and 0.295 g/l (dilutions from stock are stock, 1:2, 1:3, 1:4, 1:5 and 1:10). Fibrinogen in the test blood samples was determined from the calibration curve using the thrombin time assay results (see below). Analysis of the data was carried out on a PC using the research software supplied by IL to go with the ACL 300R coagulometer.

Thrombin time

A standard kit was used with the modification that thrombin was made up with 100 mmol $CaCl_2$ to a conc of 3 NIHU/ml. The assay was performed using research mode (i.e clot cycle 1) settings—volumes of sample and reagent 75 μl, activation time 180 sec, inter ramp interval 1 sec, acquisition time 300 sec, speed 1200 rpm. Analysis using the Path matt.def (S/RX100.S4.S4.threshold (3.50)).

---

We claim:

1. A product containing a plasminogen activator and a thrombin-activatable plasminogen analogue, for simultaneous or sequential use in thrombolytic therapy.

2. A method of treating a patient in need of thrombolytic or antithrombotic therapy, which comprises the simultaneous or sequential intravenous administration of effective amounts of a plasminogen activator and a thrombin-activatable plasminogen analogue.

3. A product as claimed in claim 1 or a method as claimed in claim 2 wherein the plasminogen activator is tPA.

4. A product as claimed in claim 1 or a method as claimed in claim 2 wherein the thrombin-activatable plasminogen analogue has a cleavage site sequence P4-P3-Pro-Arg-P1'-P2' where P3 is a basic amino acid residue, P4 is a hydrophobic amino acid residue and each of P1' and P2' is independently a non-acidic amino acid residue, said site being cleavable by thrombin between Arg and P1'.

5. A product or a method or a use as claimed in claim 4, wherein the thrombin-activatable plasminogen analogue for use in the invention is BB-10153 (SEQ ID.1).

* * * * *

UNITED STATES PATENT AND TRADEMARK OFFICE
CERTIFICATE OF CORRECTION

PATENT NO. : 5,741,771
DATED : April 21, 1998
INVENTOR(S) : Keith Dawson, Lars Michael Wood and Michael Berisford Comer It is certified that error appears in the above-identified patent and that said Letters Patent is hereby corrected as shown below:

At Col. 4, line 2, change "lie" to --Ile--.

At Col. 4, line 18, change "PI'" to --P1'--.

At Col. 4, line 26, change "lie" to read Ile--

At Col. 4, line 26, change "Iccp" to read --loop--.

At Col. 4, line 59, change "Coil" to read --Coll--.

At Col. 4, line 63, change "Coil" to read --Coll--.

At Col. 6, line 45, change "lilac" to read--ilac--

At Col. 6, line 46, change "lilac" to read--iliac--
At Col. 6, line 32, change "lilac" to--iliac--.

Signed and Sealed this

Third Day of November, 1998

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 814 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Met  Glu  His  Lys  Glu  Val  Val  Leu  Leu  Leu  Leu  Leu  Phe  Leu  Lys  Ser
-19            -15                           -10                         -5

Gly  Gln  Gly  Glu  Pro  Leu  Asp  Asp  Tyr  Val  Asn  Thr  Gln  Gly  Ala  Ser
                1              5                        10

Leu  Phe  Ser  Val  Thr  Lys  Lys  Gln  Leu  Gly  Ala  Gly  Ser  Ile  Glu  Glu
          15             20                       25

Cys  Ala  Ala  Lys  Cys  Glu  Glu  Asp  Glu  Glu  Phe  Thr  Cys  Arg  Ala  Phe
30                  35                       40                            45

Gln  Tyr  His  Ser  Lys  Glu  Gln  Gln  Cys  Val  Ile  Met  Ala  Glu  Asn  Arg
               50                      55                        60

Lys  Ser  Ser  Ile  Ile  Ile  Arg  Met  Arg  Asp  Val  Val  Leu  Phe  Glu  Lys
               65                  70                       75

Lys  Val  Tyr  Leu  Ser  Glu  Cys  Lys  Thr  Gly  Asn  Gly  Lys  Asn  Tyr  Arg
```

|     |     |     |     |     | 80  |     |     |     | 85  |     |     |     | 90  |     |     |
|-----|-----|-----|-----|-----|-----|-----|-----|-----|-----|-----|-----|-----|-----|-----|-----|

Gly Thr Met Ser Lys Thr Lys Asn Gly Ile Thr Cys Gln Lys Trp Ser
    95                  100                 105

Ser Thr Ser Pro His Arg Pro Arg Phe Ser Pro Ala Thr His Pro Ser
110             115             120                 125

Glu Gly Leu Glu Glu Asn Tyr Cys Arg Asn Pro Asp Asn Asp Pro Gln
                130             135             140

Gly Pro Trp Cys Tyr Thr Thr Asp Pro Glu Lys Arg Tyr Asp Tyr Cys
            145             150             155

Asp Ile Leu Glu Cys Glu Glu Cys Met His Cys Ser Gly Glu Asn
        160             165             170

Tyr Asp Gly Lys Ile Ser Lys Thr Met Ser Gly Leu Glu Cys Gln Ala
    175             180             185

Trp Asp Ser Gln Ser Pro His Ala His Gly Tyr Ile Pro Ser Lys Phe
190             195             200                 205

Pro Asn Lys Asn Leu Lys Lys Asn Tyr Cys Arg Asn Pro Asp Arg Glu
                210             215             220

Leu Arg Pro Trp Cys Phe Thr Thr Asp Pro Asn Lys Arg Trp Glu Leu
            225             230             235

Cys Asp Ile Pro Arg Cys Thr Thr Pro Pro Pro Ser Ser Gly Pro Thr
        240             245             250

Tyr Gln Cys Leu Lys Gly Thr Gly Glu Asn Tyr Arg Gly Asn Val Ala
    255             260             265

Val Thr Val Ser Gly His Thr Cys Gln His Trp Ser Ala Gln Thr Pro
270             275             280                 285

His Thr His Asn Arg Thr Pro Glu Asn Phe Pro Cys Lys Asn Leu Asp
                290             295             300

Glu Asn Tyr Cys Arg Asn Pro Asp Gly Lys Arg Ala Pro Trp Cys His
            305             310             315

Thr Thr Asn Ser Gln Val Arg Trp Glu Tyr Cys Lys Ile Pro Ser Cys
        320             325             330

Asp Ser Ser Pro Val Ser Thr Glu Gln Leu Ala Pro Thr Ala Pro Pro
    335             340             345

Glu Leu Thr Pro Val Val Gln Asp Cys Tyr His Gly Asp Gly Gln Ser
350             355             360                 365

Tyr Arg Gly Thr Ser Ser Thr Thr Thr Thr Gly Lys Lys Cys Gln Ser
                370             375             380

Trp Ser Ser Met Thr Pro His Arg His Gln Lys Thr Pro Glu Asn Tyr
            385             390             395

Pro Asn Ala Gly Leu Thr Met Asn Tyr Cys Arg Asn Pro Asp Ala Asp
        400             405             410

Lys Gly Pro Trp Cys Phe Thr Thr Asp Pro Ser Val Arg Trp Glu Tyr
    415             420             425

Cys Asn Leu Lys Lys Cys Ser Gly Thr Glu Ala Ser Val Val Ala Pro
430             435             440                 445

Pro Pro Val Val Leu Leu Pro Asp Val Glu Thr Pro Ser Glu Glu Asp
                450             455             460

Cys Met Phe Gly Asn Gly Lys Gly Tyr Arg Gly Lys Arg Ala Thr Thr
            465             470             475

Val Thr Gly Thr Pro Cys Gln Asp Trp Ala Ala Gln Glu Pro His Arg
        480             485             490

His Ser Ile Phe Thr Pro Glu Thr Asn Pro Arg Ala Gly Leu Glu Lys
    495             500             505

-continued

| | | | | | | | | | | | | | |
|---|---|---|---|---|---|---|---|---|---|---|---|---|---|
| Asn 510 | Tyr | Cys | Arg | Asn | Pro 515 | Asp | Gly | Asp | Val | Gly 520 | Gly | Pro | Trp | Cys | Tyr 525 |
| Thr | Thr | Asn | Pro | Arg 530 | Lys | Leu | Tyr | Asp | Tyr 535 | Cys | Asp | Val | Pro | Gln 540 | Cys |
| Ala | Ala | Pro | Ser 545 | Phe | Asp | Cys | Gly | Lys 550 | Pro | Gln | Val | Glu | Pro 555 | Lys | Lys |
| Cys | Thr | Thr 560 | Lys | Ile | Lys | Pro | Arg 565 | Ile | Val | Gly | Gly | Cys 570 | Val | Ala | His |
| Pro | His 575 | Ser | Trp | Pro | Trp | Gln 580 | Val | Ser | Leu | Arg | Thr 585 | Arg | Phe | Gly | Met |
| His 590 | Phe | Cys | Gly | Gly | Thr 595 | Leu | Ile | Ser | Pro | Glu 600 | Trp | Val | Leu | Thr | Ala 605 |
| Ala | His | Cys | Leu | Lys 610 | Lys | Ser | Pro | Arg | Pro 615 | Ser | Ser | Tyr | Lys | Val 620 | Ile |
| Leu | Gly | Ala | His 625 | Gln | Lys | Val | Asn | Leu 630 | Glu | Pro | His | Val | Gln 635 | Glu | Ile |
| Glu | Val | Ser 640 | Arg | Leu | Phe | Leu | Glu 645 | Pro | Thr | Arg | Lys | Asp 650 | Ile | Ala | Leu |
| Leu | Lys 655 | Leu | Ser | Ser | Pro | Ala 660 | Val | Ile | Thr | Asp | Lys 665 | Val | Ile | Pro | Ala |
| Cys 670 | Leu | Pro | Ser | Pro | Asn 675 | Tyr | Val | Val | Ala | Asp 680 | Arg | Thr | Glu | Cys | Phe 685 |
| Ile | Thr | Gly | Trp | Gly 690 | Glu | Thr | Gln | Gly | Thr 695 | Phe | Gly | Ala | Gly | Leu 700 | Leu |
| Lys | Glu | Ala | Gln 705 | Leu | Pro | Val | Ile | Glu 710 | Asn | Lys | Val | Cys | Asn 715 | Arg | Tyr |
| Glu | Phe | Leu 720 | Asn | Gly | Arg | Val | Gln 725 | Ser | Thr | Glu | Leu | Cys 730 | Ala | Gly | His |
| Leu | Ala 735 | Gly | Gly | Thr | Asp | Ser 740 | Cys | Gln | Gly | Asp | Ser 745 | Gly | Gly | Pro | Leu |
| Val 750 | Cys | Phe | Glu | Lys | Asp 755 | Lys | Tyr | Ile | Leu | Gln 760 | Gly | Val | Thr | Ser | Trp 765 |
| Gly | Leu | Gly | Cys | Ala 770 | Arg | Pro | Asn | Lys | Pro 775 | Gly | Val | Tyr | Val | Arg 780 | Val |
| Ser | Arg | Phe | Val 785 | Thr | Trp | Ile | Glu | Gly 790 | Val | Met | Arg | Asn | Asn 795 | | |